US012796996B2

(12) United States Patent
To et al.

(10) Patent No.: US 12,796,996 B2
(45) Date of Patent: Nov. 17, 2026

(54) METHODS, SYSTEMS, AND APPARATUS FOR SIMULATING THE CHANGE OF CHEST IMPEDANCE WITH PASSIVE COMPONENTS AND ELECTROCARDIOGRAM CONTAMINATION

(71) Applicant: KONINKLIJKE PHILIPS N.V., Eindhoven (NL)

(72) Inventors: Lok Yiu To, Bothell, WA (US); Joseph Diederichs, Bothell, WA (US); Alan Paul Greenstein, Bothell, WA (US); Chenguang Liu, Bothell, WA (US); Christopher Neils, Bothell, WA (US); Dawn Jorgenson, Bothell, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 860 days.

(21) Appl. No.: 18/015,098

(22) PCT Filed: Jun. 29, 2021

(86) PCT No.: PCT/EP2021/067879
§ 371 (c)(1),
(2) Date: Jan. 9, 2023

(87) PCT Pub. No.: WO2022/008301
PCT Pub. Date: Jan. 13, 2022

(65) Prior Publication Data

US 2023/0255537 A1 Aug. 17, 2023

Related U.S. Application Data

(60) Provisional application No. 63/049,155, filed on Jul. 8, 2020.

(51) Int. Cl.
*A61N 1/39* (2006.01)
*A61B 5/319* (2021.01)
(Continued)

(52) U.S. Cl.
CPC ................ *A61B 5/319* (2021.01); *A61B 5/33* (2021.01); *A61N 1/39044* (2017.08); *A61N 1/3993* (2013.01); *H01C 10/10* (2013.01)

(58) Field of Classification Search
CPC .. A61B 5/319; A61N 1/39044; A61N 1/3993; H01C 10/10; H01C 10/14
See application file for complete search history.

(56) References Cited

U.S. PATENT DOCUMENTS

| | | | | |
|---|---|---|---|---|
| 4,611,998 A * | 9/1986 | Ramamurthy | ....... | G09B 23/288 434/265 |
| 4,654,626 A | 3/1987 | Carsello | | |

(Continued)

FOREIGN PATENT DOCUMENTS

| | | |
|---|---|---|
| KR | 100673060 B1 | 1/2007 |

OTHER PUBLICATIONS

Holmberg, M. et al., (2000). "Incidence, duration and survival of ventricular fibrillation in out-of-hospital cardiac arrest patients in Sweden." Resuscitation,44(1), 7-17. doi:10.1016/s0300-9572(99)00155-0.

(Continued)

*Primary Examiner* — George R Evanisko

(57) ABSTRACT

An electromechanical system for generating a CPR-corrupted ECG signal is provided. The electromechanical system may include an ECG signal generator electrically coupled to a first contact of an AED. The electromechanical system may further include a potentiometer electrically coupled to the ECG signal generator and a second contact of the AED. The electromechanical system may further include a compression mechanism. The compression mechanism may be configured to receive a vertical force and adjust an impedance of the potentiometer according to the vertical force. The compression mechanism may include a rack having a plurality of teeth and an initial position. The rack (Continued)

may be configured to translate to a second position according to the vertical force. The compression mechanism may further include a gear with a plurality of teeth engaged with the teeth of the rack such that the gear rotates according to the translation of the rack.

13 Claims, 6 Drawing Sheets

(51) Int. Cl.
*A61B 5/33* (2021.01)
*H01C 10/10* (2006.01)

(56) References Cited

U.S. PATENT DOCUMENTS

| | | | |
|---|---|---|---|
| 4,915,635 A | 4/1990 | Ingenito | |
| 4,932,879 A | 6/1990 | Ingenito | |
| 5,391,081 A | 2/1995 | Lampotang | |
| 8,820,158 B2 | 9/2014 | Oike | |
| 9,633,577 B2 | 4/2017 | Constantine | |
| 2013/0023781 A1 | 1/2013 | Freeman | |
| 2014/0093853 A1* | 4/2014 | Constantine, III | G09B 23/288 434/265 |

OTHER PUBLICATIONS

Amann, A. et al., (2010). "Reduction of CPR artifacts in the ventricular fibrillation ECG by coherent line removal." BioMedical Engineering OnLine,9(1), 2. doi:10.1186/1475-925x-9-2.

International Search Report for PCT/EP2021/067879 filed Jun. 29, 2021.

* cited by examiner

METHODS, SYSTEMS, AND APPARATUS FOR SIMULATING THE CHANGE OF CHEST IMPEDANCE WITH PASSIVE COMPONENTS AND ELECTROCARDIOGRAM CONTAMINATION

This application is a national stage application under 35 U.S.C. § 371 of International Application No. PCT/EP2021/067879 filed on Jun. 29, 2021 and published in the English language on Jan. 13, 2022 as International Publication No. WO2022/008301, which claims priority to U.S. Patent Application No. 63/049,155 filed on Jul. 8, 2020, the entire disclosures of which are incorporated herein by reference.

FIELD OF THE DISCLOSURE

The present disclosure is directed generally to systems for simulating cardio-pulmonary resuscitation (CPR) contamination of electrocardiogram signals.

BACKGROUND

Patient physiological signal simulation is commonly used in the medical community (e.g. manufacturers, hospitals, research facilities) to reproduce real-life scenarios for creating new devices and algorithms, or as training tools for physicians and/or paramedics to acquire realistic experience in a controlled environment. In the realm of electrocardiogram (ECG) signals, Automatic External Defibrillator (AED) manufacturers obtain field data from their distributed AEDs, but the collected data is often corrupted or noisy. This noise and/or corruption may be caused by numerous factors, such as patients' physiological status, environment factors, pad imbalance, etc. In addition, acquiring such patient data may require a high degree of administrative work.

Currently, AED users, mainly paramedics and emergency medical personnel, often ignore voice prompts from the device because of either a conflict between the AED audio instruction and their current medical practices or confusion with the use of the device. Thus, AED users continue to perform CPR during an analyzing period. As a result, the ECG analysis algorithm may not accurately identify the ECG rhythm and consequently delays defibrillation therapy. This delay can significantly impact patient survival rate and recovery. Moreover, it is difficult to generate and collect sample data, and the collected data usually contain undesired artifacts, adding levels of sophistication and impeding the development of algorithms.

There have been efforts in developing more realistic biosignals during CPR, but such signals have been digitally simulated. Digital simulation typically ignores some of the stochastic nature of the signal and reduces the realism of the signal. Therefore, there is a need for simulation devices that can accurately and consistently replicate ECG and impedance signals undergoing physiological changes due to CPR.

SUMMARY OF THE DISCLOSURE

The present disclosure is generally directed to CPR-artifact simulation systems, methods, and apparatus. These systems may serve as usability-testing tools for new algorithms by contaminating simulated ECG signals in a manner representative of how CPR changes a body's thoracic impedance. Currently, heart-rhythm simulation devices may generate a large variety of noise-free ECG waveforms. However, a robust algorithm requires corrupted signals that closely resemble real-life situations. The disclosed systems can generate both corrupted ECG signals and impedance signals, resembling all possible signals by the AED. Furthermore, by using only analog systems, this invention can produce realistic CPR corrupted ECG signals that physically correlate with the impedance signal being recorded on the system. Additionally, the disclosed analog systems provide greater versatility than corresponding digital systems. The analog systems may be implemented with other simulation systems, simulation devices, or manikins without the complexity of digital interfacing, as analog interfacing may be achieved through a simple adapter.

Generally, in one aspect, an electrical system, method, and apparatus for generating a CPR-corrupted ECG signal is provided. The electrical system may include an ECG signal generator electrically coupled to a first contact of an AED. The electrical system may further include a backend circuit. The backend circuit may include a potentiometer. The potentiometer may be electrically coupled to the ECG signal generator and a second contact of the AED. A user input is configured to adjust an impedance of the potentiometer.

According to an example, the backend circuit may further include a divider impedance circuit electrically coupled to the potentiometer. The divider impedance circuit may form a voltage divider circuit with the potentiometer. The backend circuit may further include a reference voltage circuit electrically coupled to the divider impedance circuit and the potentiometer.

According to an example, the divider impedance circuit may include one or more resistors.

According to an example, the reference voltage circuit may include a DC voltage source.

According to an example, the reference voltage circuit may further include a regulator circuit. The regulator circuit may be a Zener diode shunt regulator circuit.

According to an example, the backend circuit may further comprise a potentiometer adjustment circuit electrically coupled in parallel to the potentiometer. The potentiometer adjustment circuit may include one or more resistors.

Generally, in another aspect, an electromechanical system, method, and apparatus for generating a CPR-corrupted ECG signal is provided. The electromechanical system may include an ECG signal generator electrically coupled to a first contact of an AED. The electromechanical system may further include a backend circuit. The backend circuit may include a potentiometer. The potentiometer may be electrically coupled to the ECG signal generator and a second contact of the AED. The electromechanical system, method, or apparatus may further include a compression mechanism. The compression mechanism may be configured to receive a vertical force. The compression mechanism may also be configured to adjust an impedance of the potentiometer according to the vertical force.

According to an example, the backend circuit may further include a divider impedance circuit electrically coupled to the potentiometer. The divider impedance circuit may form a voltage divider circuit with the potentiometer. The backend circuit may further include a reference voltage circuit electrically coupled to the divider impedance circuit and the potentiometer.

According to an example, the compression mechanism may include a rack having a plurality of teeth and an initial position. The rack may be configured to translate to a second position according to the vertical force. The compression mechanism may further include a gear with a plurality of teeth engaged with the teeth of the rack such that the gear rotates according to the translation of the rack.

According to an example, the rack may be configured to translate from the second position to the initial position after the application of the vertical force.

According to an example, the potentiometer may be a rotary potentiometer having a shaft coupled to the gear such that the rotation of the gear adjusts the impendence of the potentiometer.

Generally, in another aspect, an electromechanical system, method, and apparatus for adjusting the impedance of a circuit is provided. The electromechanical system may include a potentiometer. The electromechanical system may include a compression mechanism. The compression mechanism may be configured to receive a vertical force. The compression mechanism may be further configured to adjust the impedance of the potentiometer according to the vertical force.

According to an example, the compression mechanism may include a rack having a plurality of teeth and an initial position. The rack may be configured to translate according to the vertical force. The compression mechanism may further include a gear with a plurality of teeth engaged with the teeth of the rack such that the gear rotates according to the translation of the rack.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

The present disclosure describes various embodiments for systems for simulating CPR corruption of ECG signals. More generally, Applicant has recognized and appreciated that it would be beneficial to provide systems to generate CPR-corrupted ECG signals using an electromechanical device to model CPR administered by a first responder. These systems may be used as a usability testing tool to validate new defibrillator algorithms, functionality, or systems by (1) recognizing the rate, depth, onset, and offset for CPR, (2) analyzing corrupted ECG rhythms during CPR, and (3) evaluating CPR quality. These systems may also be used to enhance functionality and quality of a manikin product for medical training and usability testing by providing a CPR-corrupted ECG signal and a thoracic impedance signal as feedback that correlates with how the CPR is being performed.

Figure 1:
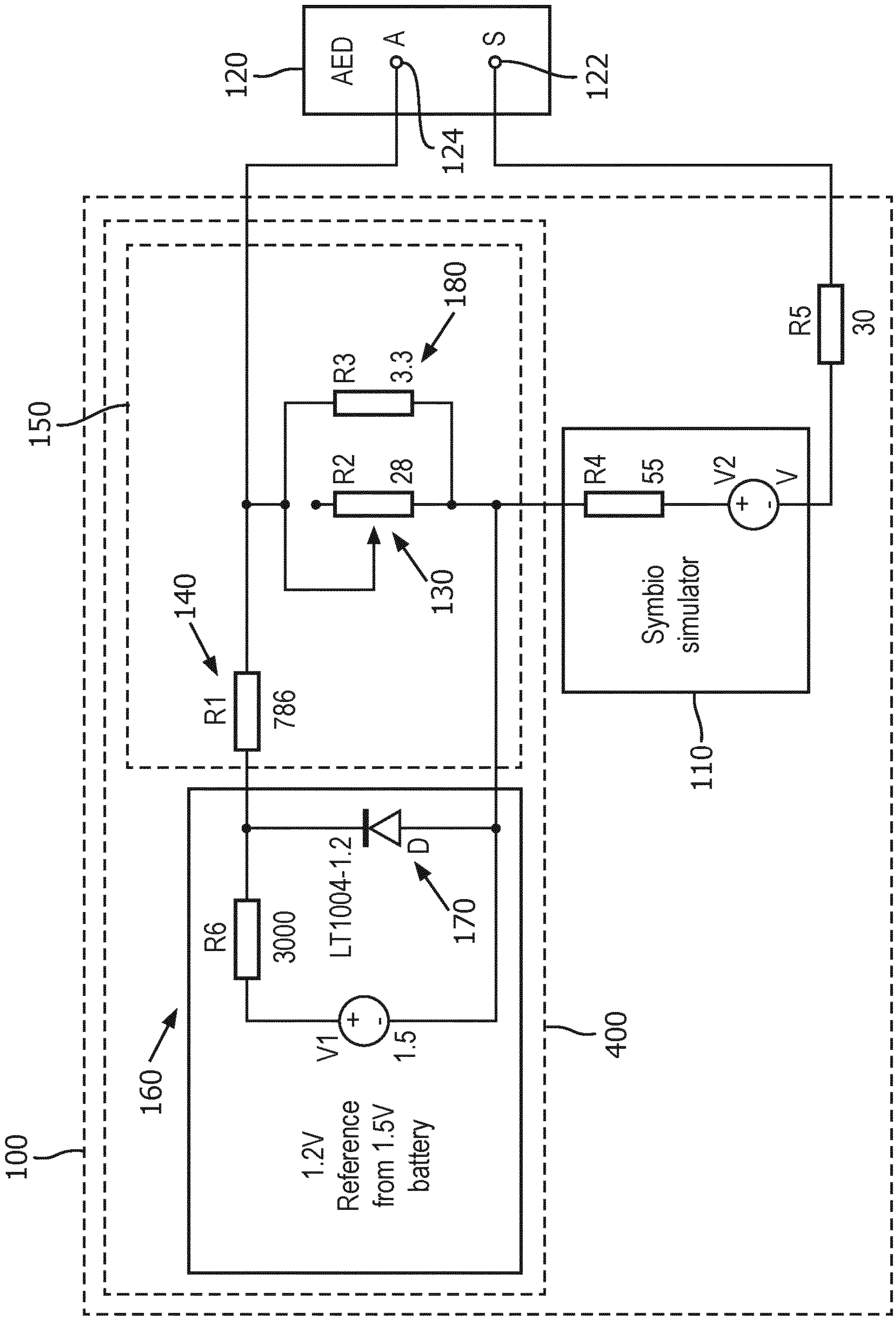
FIG. 1 is a circuit schematic of an electrical system for generating a CPR-corrupted ECG signal, in accordance with an example.

Referring to FIG. 1, in a one aspect, an electrical system 100 for generating a CPR-corrupted ECG signal is provided. The electrical system 100 may include an ECG signal generator 110 electrically coupled to a first contact 122 of an AED 120. The ECG signal 110 generator may have an internal impedance of 55 ohms.

The electrical system 100 may further include a backend circuit 400. The backend circuit 400 may include a potentiometer 130. Potentiometer 130 is shown in FIG. 1 as R2. The potentiometer 130 may be electrically coupled to the ECG signal generator 110 and a second contact 124 of the AED 120. The potentiometer 130 may be a rotary potentiometer. In further examples, the potentiometer 130 may be a sliding potentiometer.

A user input 250 is configured to adjust an impedance of the potentiometer 130. In an example explained in greater detail below, the user input 250 may be downward thrust as would be performed by a first responder during CPR. A device, such as a compression mechanism 190 described in greater detail below, may then adjust the impedance of the rotary potentiometer by actuating its shaft. The potentiometer 130 may have an impedance range from 0 to 30 ohms. In one example, and as shown in FIG. 1, the potentiometer 130 is set to 28 ohms. In one example, the impendence of the potentiometer 130 and its related circuitry is adjusted such that an impedance signal of the backend circuit 400 has a baseline of 90 ohms and an oscillation range of 4 ohms.

According to an example, the backend circuit 400 may further include a divider impedance circuit 140 electrically coupled to the potentiometer 130. The divider impedance circuit 140 may include one or more resistors. The one or more resistors may in serial and/or parallel configuration. As shown in FIG. 1, the divider impendence circuit 140 may be R1, a 786 ohm resister. The divider impedance circuit 140 may form a voltage divider circuit 150 with the potentiometer 130.

The backend circuit 400 may further include a reference voltage circuit 160 electrically coupled to the divider impedance circuit 140 and the potentiometer 130. The reference voltage circuit 160 may include a DC voltage source. The reference voltage circuit may further include a regulator circuit 170. The regulator circuit may be a Zener diode shunt regulator circuit. In an example shown in FIG. 1, DC voltage source V1 provides a voltage of 1.5 V. The Zener diode shunt circuit includes a single Zener diode D. D, embodied as Linear Technology part number LT1004-1.2, has a reverse breakdown voltage of 1.2 V. Thus, arranged as a Zener diode shunt regulator, D maintains the output voltage of reference voltage circuit 160 as approximately 1.2 V. The regulator circuit 170 of FIG. 1 further includes current limiting resistor R6. In this example, R6 is set to 3000 ohms.

According to an example, the backend circuit may further comprise a potentiometer adjustment circuit 180 electrically coupled in parallel to the potentiometer 130. The potentiometer adjustment circuit 180 may include one or more resistors. In the example shown in FIG. 1, the potentiometer adjustment circuit 180 is embodied as resister R3 with an impedance of 3.3 ohms. Modifying the impedance of the potentiometer adjust circuit 180 allows for greater control of the overall impedance of the backend circuit 400 as controlled by the potentiometer 130. In other examples, the potentiometer 130 may be a plurality of resistors in a series and/or parallel configuration.

In a further example, the electrical system 100 may further include an overvoltage circuit to protect the backend circuit 400 during the application of electric shock in defibrillation. In an example, the overvoltage circuit may include a gas discharge tube (GDT) and/or a transient voltage suppressor (TVS). In the event of delivering an electric shock into the system, the GDT and/or TVS may be activated to shunt excess transient current back to the AED 120 to reduce excess current in the backend circuit 400. In an example, the ECG signal generator 110 may be designed to withstand normal defibrillation without damage to its internal components. In this way, the ECG signal generator 110 may be used to reduce the electrical load on the other electrical components of the circuit.

As described above, FIG. 1 shows a sample circuit diagram for the electrical system 100. The resister values shown for R1-R6 are example values used in a prototype of the electrical system 100. A person having ordinary skill in the art would appreciate that other resister values may be possible, or even preferred, depending on the application. As the R2 resistance value changes according to the setting of the potentiometer 130, the overall impedance change of the system 100 may be calculated using equation 1 below:

$$\Delta Z = \frac{\Delta R_2 R_3}{R_2 + R_3} \tag{1}$$

Further, the change in the output voltage level of the system 100 may be calculated as equation 2 below:

$$\Delta V_{out} = \frac{V_1\left(\frac{\Delta R_2 R_3}{R_2 + R_3}\right)}{R_1 + \frac{\Delta R_2 R_3}{R_2 + R_3}} \tag{2}$$

Figure 2A:
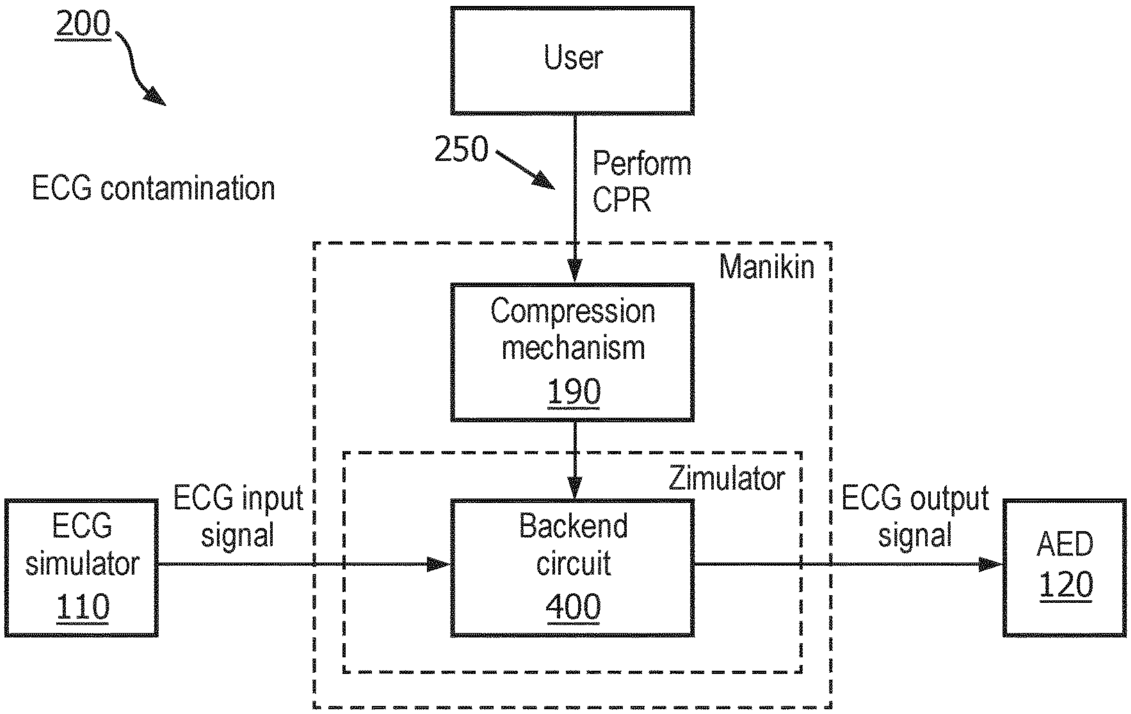
FIG. 2A is a block diagram schematic of an electromechanical system for generating a CPR-corrupted ECG signal, in accordance with an example.

Referring to FIG. 2A, generally, in another aspect, an electromechanical system 200 for generating a CPR-corrupted ECG signal is provided. The electromechanical system 200 may include an ECG signal generator 110 electrically coupled to a first contact 122 of an AED 120.

The electromechanical system 200 may further include a backend circuit 400. The backend circuit 400 may include a potentiometer 130. The potentiometer 130 may be electrically coupled to the ECG signal generator 110 and a second contact 124 of the AED 124.

The electromechanical system 200 may further include a compression mechanism 190. The compression mechanism 190 may be configured to receive a vertical force, such as a downward thrust as would be performed by a first responder during CPR. The compression mechanism 190 may also be configured to adjust an impedance of the potentiometer 130 according to the vertical force.

Figure 3A:
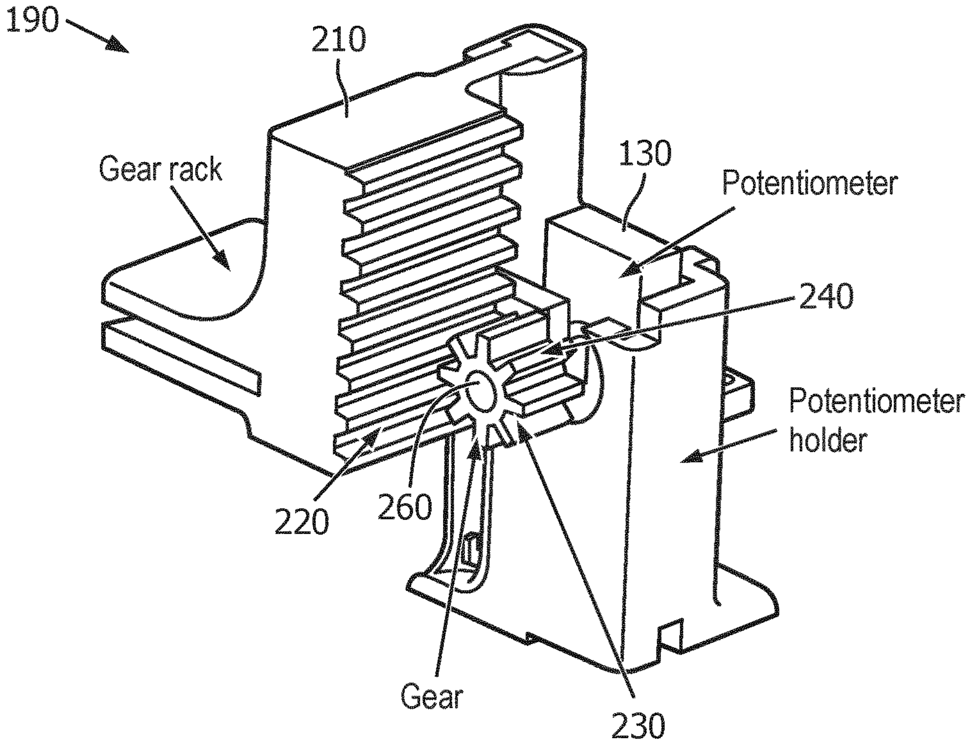
FIG. 3A is an isometric drawing of a compression mechanism for adjusting the impedance of a potentiometer, in accordance with an example.
Figure 3B:
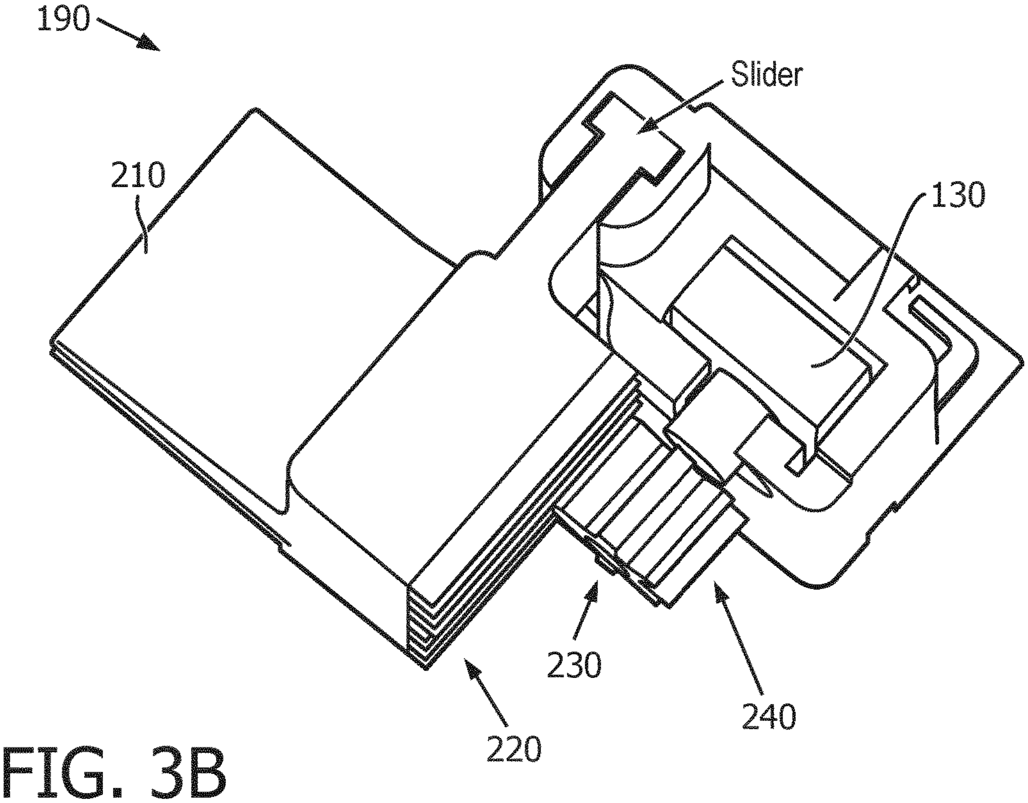
FIG. 3B is a top view drawing of a compression mechanism for adjusting the impedance of a potentiometer, in accordance with an example.

Referring to FIGS. 3A and 3B, the compression mechanism 190 may include a rack 210 having a plurality of teeth 220 and an initial position. The rack 210 may be configured to translate to a second position according to the vertical force. The compression mechanism 190 may further include a gear 230 with a plurality of teeth 240 engaged with the teeth 220 of the rack 210 such that the gear 230 rotates according to the translation of the rack 210.

According to an example, the potentiometer 130 may be a wire-wound, rotary potentiometer having a shaft 260 coupled to the gear 230 such that the rotation of the gear 230 adjusts the impendence of the potentiometer 230. The potentiometer 130 may have a rotational range of 300 degrees. In an example configuration, a 5 cm translation of the rack 210 may result in 1 ohm of impedance change due to rotation of the shaft 260 of the potentiometer 230. The amount of impedance change per distance of rack translation may be controlled by a variety of factors including, but not limited to, the diameter of the gear 230, the impedance range of the potentiometer 130, and/or the impedance of the potentiometer adjustment circuit 180.

To facilitate the rotation of the shaft 260 of the potentiometer 130, the potentiometer 130 may sit in a potentiometer holder, as shown in FIGS. 3A and 3B. As further shown in FIG. 3B, the rack 210 may include a slider configured to engage with a slot in the potentiometer holder. This configuration may provide proper alignment of the components of the compression mechanism 190, including the potentiometer 130, gear 230, and rack 210. These components may be produced via 3D printing, and may be composed of polylactic acid (PLA). In other examples, nylon may be used to reduce friction between the components.

The rack 210 may be further configured to translate from the second position to the initial position after the application of the vertical force. This reflex response may be configured to mimic decompression of the human thorax during CPR following a downward thrust. In other embodiments, the rack 210 may be configured to translate from the second position to a third position, wherein the third position differs from the initial position.

According to an example, the backend circuit 400 may further include a divider impedance circuit 140 electrically coupled to the potentiometer 130. The divider impedance circuit 140 may form a voltage divider circuit 150 with the potentiometer 130. The backend circuit 400 may further include a reference voltage circuit 160 electrically coupled to the divider impedance circuit 140 and the potentiometer 130.

Figure 2B:
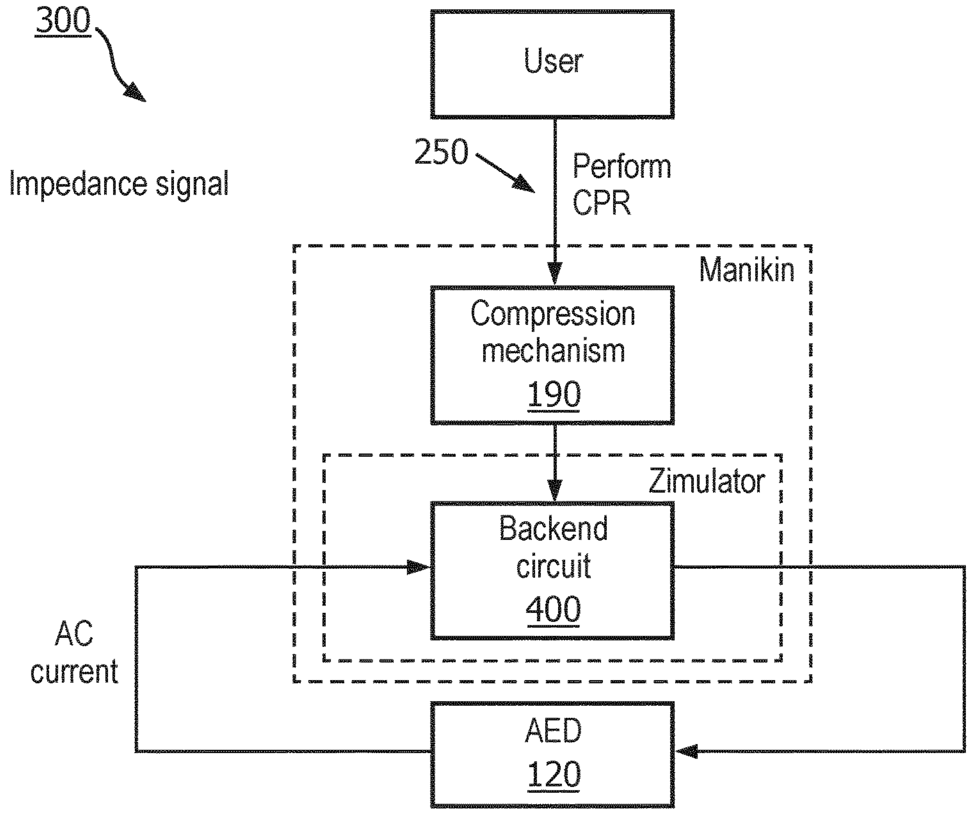
FIG. 2B is a block diagram of an electromechanical system for adjusting the impedance of a circuit, in accordance with an example.

Referring to FIG. 2B, generally, in another aspect, an electromechanical system 300 for adjusting the impedance of a circuit is provided. The electromechanical system 300 may include a potentiometer 130. The electromechanical system 300 may include a compression mechanism 190. The compression mechanism 190 may be configured to receive a vertical force. The compression mechanism 190 may be further configured to adjust the impedance of the potentiometer 130 according to the vertical force. The compression mechanism 190 may include a rack 210 having a plurality of teeth 220 and an initial position. The rack 210 may be configured to translate according to the vertical force. The compression mechanism 190 may further include a gear 230 with a plurality of teeth 240 engaged with the teeth 220 of the rack 210 such that the gear 230 rotates according to the translation of the rack 210.

According to an example, the potentiometer 130 may be a wire-wound, rotary potentiometer having a shaft 260 coupled to the gear 230 such that the rotation of the gear 230 adjusts the impendence of the potentiometer 130. The potentiometer 130 may have a rotational angle of 300 degrees.

The electromechanical system 300 may be configured to be installed in a manikin. Rack 210 may be clipped onto a plastic arch of a rib-piece of the manikin. When a user performs CPR on the manikin, the rib-piece and plastic arch may be pushed down so as to also slide the rack 210 down the potentiometer holder. The potentiometer holder may be secured in the manikin using epoxy.

To protect the potentiometer 130 from over-rotation, the electromechanical system 300 does not utilize the full rotation of the rotary potentiometer. In one example, the compression system 190 allows for 280 degree rotation of the gear 210 and the shaft 260 of the potentiometer 130.

Figure 4:
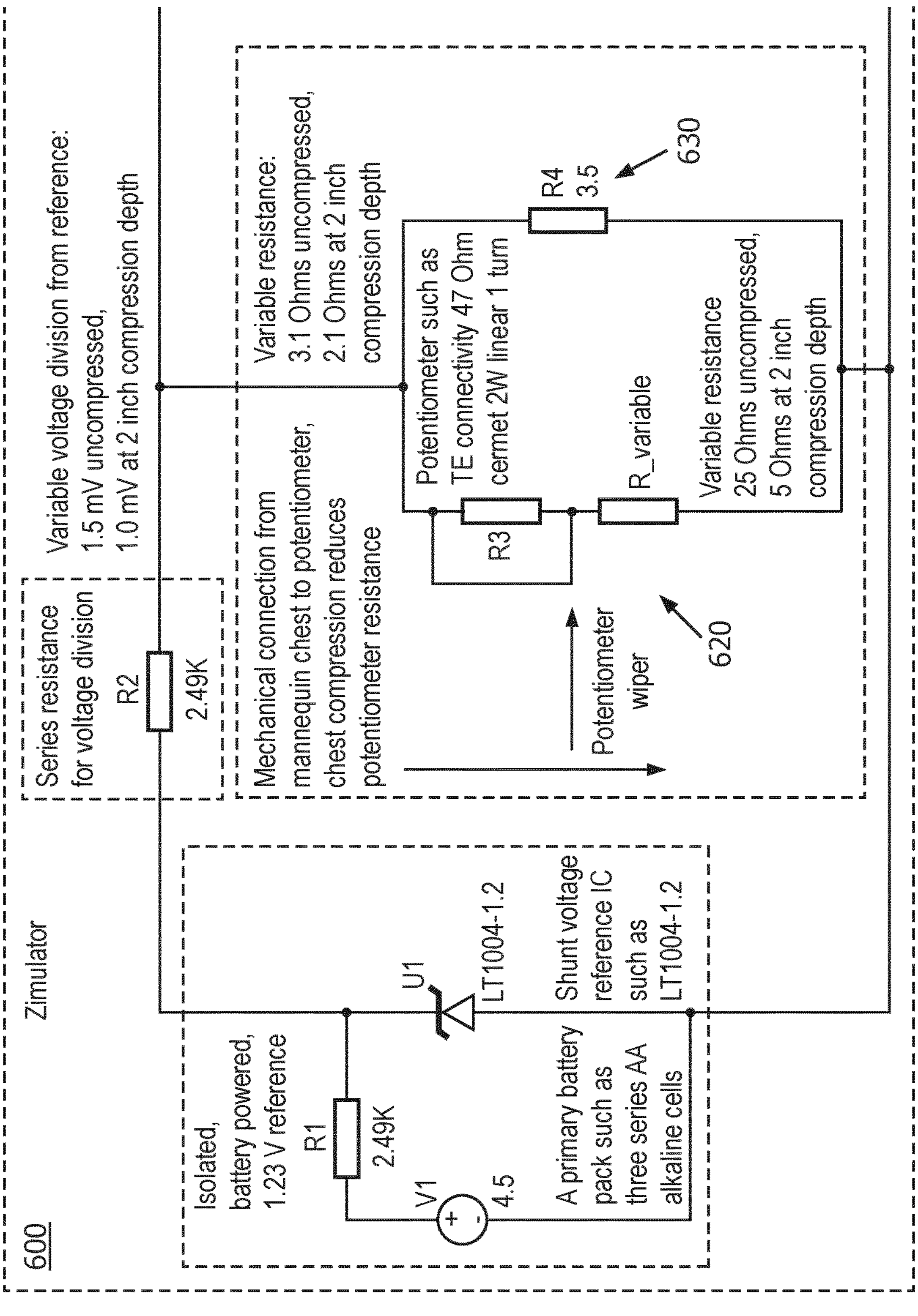
FIG. 4 is a circuit schematic of an electrical system for generating a CPR-corrupted ECG signal, in accordance with a further example.
Figure 4:
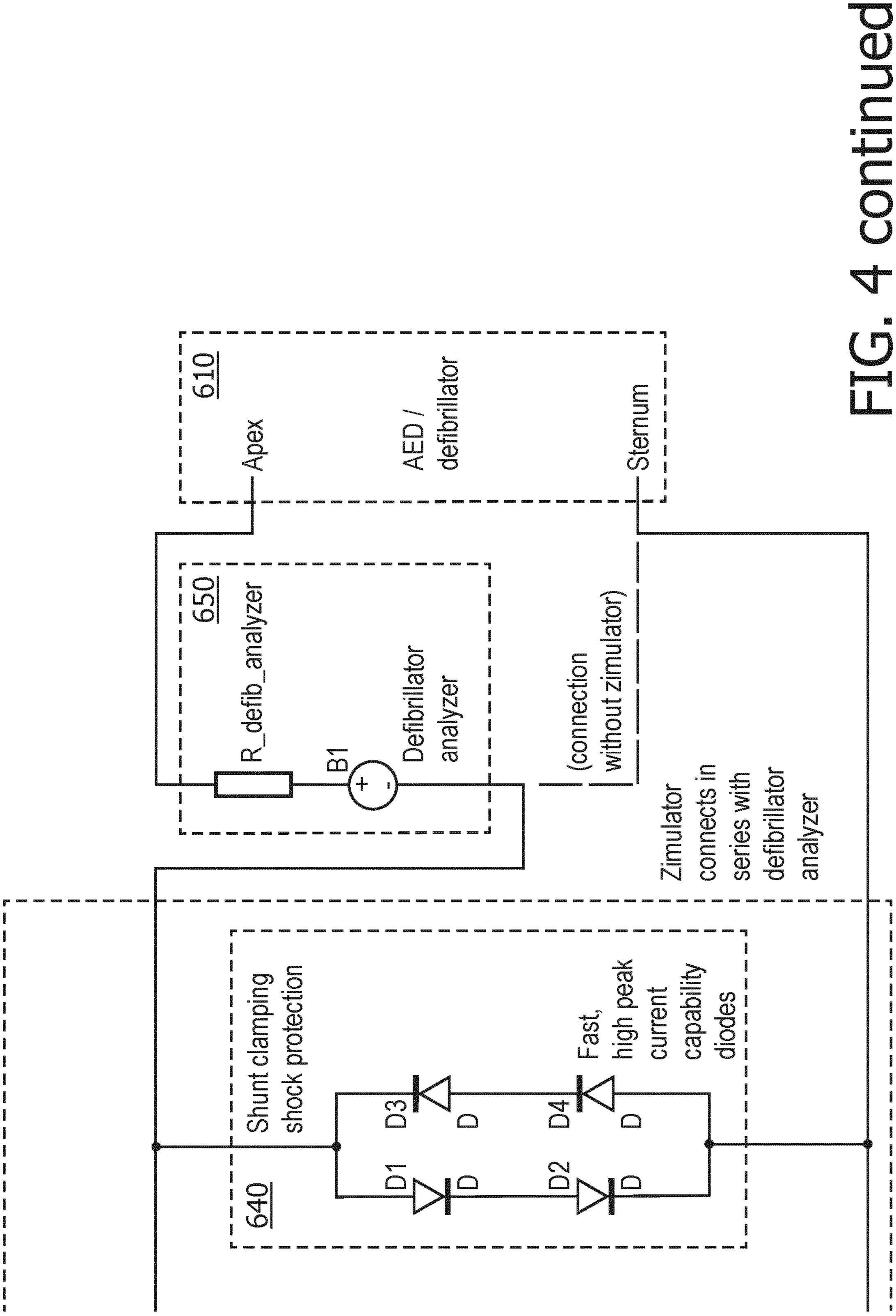

Referring to FIG. 4, generally, in another aspect, a further example of an electrical system 600 for generating a CPR-corrupted ECG signal is provided. FIG. 4 shows a schematic diagram for the further system 600. An AED or defibrillator 610 performing ECG analysis is found on the right side of FIG. 4. Without the system 600, the AED 610 would be connected directly to a Defibrillator Analyzer 650, which presents a cardiac rhythm voltage source in series with a patient resistance. Some defibrillator analyzers 650 are designed to be shockable by the AED 610 as well.

The system 600 is connected in series with a defibrillator analyzer 650 in order to sum voltage and resistance variations into a signal from the defibrillator analyzer 650 seen by the AED 610. With a standard 2 inch CPR compression stroke on a CPR mannequin chest, the system 600 shown is designed to add 0.5 mV peak-to-peak to the signal from the defibrillator analyzer 650, with the added voltage dependent on the instantaneous depth of a CPR compression stroke. The system 600 shown is also designed to add 1 ohm peak-to-peak to the resistance presented by the defibrillator analyzer 650, with an analogous dependence on the CPR stroke. The voltage and resistance variations are designed to be correlated.

As described above, the means of conversion of mechanical motion of the CPR mannequin chest to an electrical variation is by way of a potentiometer 620. The instantaneous resistance value of the potentiometer 620, in parallel with another passive resistor 630 to lower the overall resistance value, serves as both the direct resistance variation of the system 600, and also as part of a voltage divider, which divides a reference voltage by a (relatively large) ratio to provide the system 600 voltage variation. As shown in FIGS. 3A and 3B, a rack and pinion style gear mechanism may be used to convert the linear motion of the mannequin chest to rotary motion of the potentiometer 620. The design values, using a potentiometer variation from 25 ohms to 5 ohms in parallel with a fixed 3.5 ohm resistance, results in a non-linear overall variation in resistance, with a slower variation over the higher end of the potentiometer 620 in comparison with the lower end deeper in the compression stroke. This may be partially compensated for by adjustments to the mechanical rack and pinion mechanism, for example, by offsetting the center of the "pinion" gear element on the potentiometer shaft, in order to provide more rotation during the early part of the compression stroke in comparison with the later part.

The system 600 also includes protection from a shock delivered by the AED 610 to the series connection of the defibrillator analyzer 650 and the system 600. The protection is in the form of shunt anti-parallel diodes 640, for bidirectional protection. The shunt diodes 640 are intended to divert a high current defibrillation pulse from the remainder of the system 600, while clamping the voltage seen by the remaining circuit to the peak forward voltage of the diodes 640 during the pulse. In normal operation (rather than during a shock event), the voltage and resistance across the shunt diodes 640 is very low, and so the shunt diodes 640 have negligible impact on the system 600.

Selection of specific appropriate diodes 640 may be left to a user, beyond guidance that the diodes 640 must be capable of handling the peak defibrillation current and overall defibrillation current pulse, and must be fast enough to conduct the defibrillation current pulse without excess instantaneous voltage during the pulse.

Figure 5:
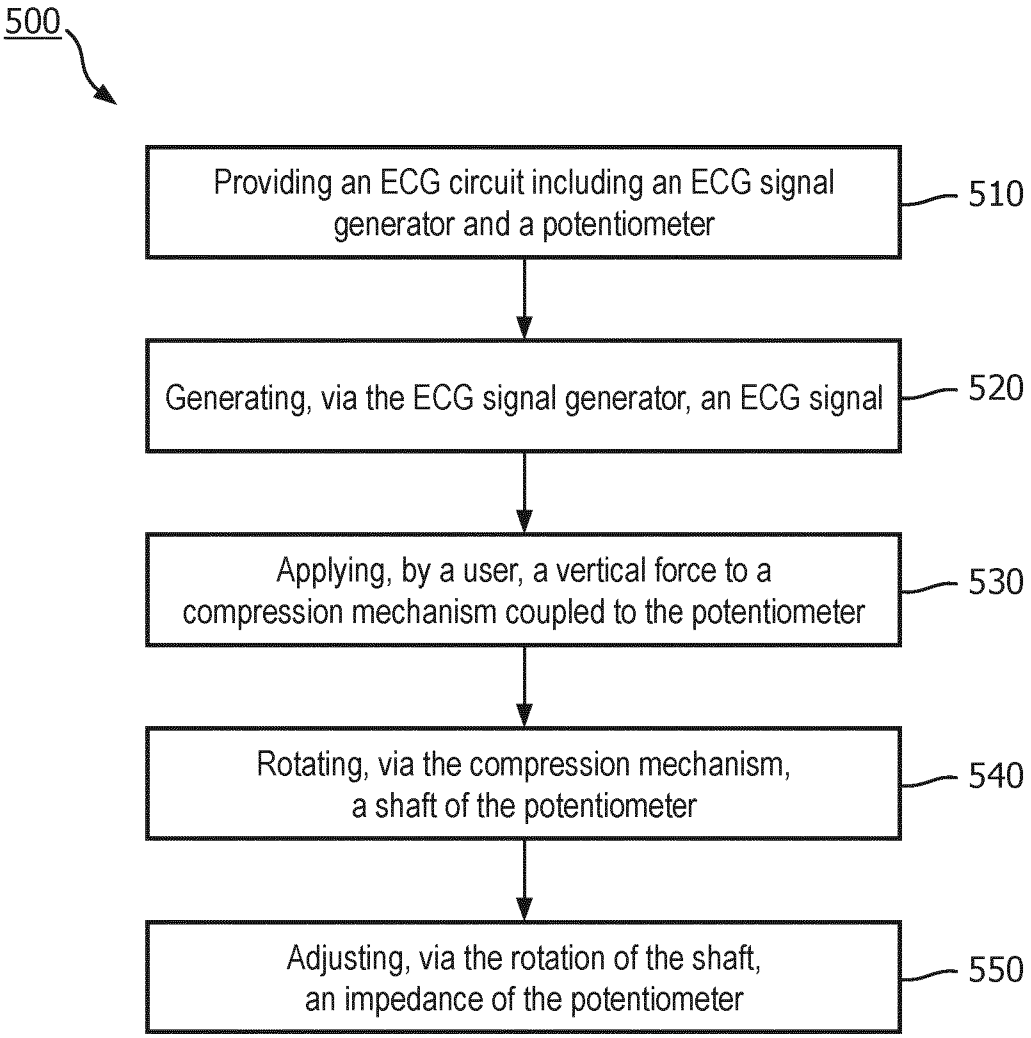
FIG. 5 is a flow chart of a method for generating a CPR-corrupted ECG signal, in accordance with an example.

Referring to FIG. 5, generally, in another aspect, a method 500 for generating a CPR-corrupted ECG signal is provided. The method 500 may include the step of providing 510 an ECG circuit including an ECG signal generator and a potentiometer. The method may include the step of generating 520, via the ECG signal generator, an ECG signal. The method may further include the step of applying 530, by a user, a vertical force to a compression mechanism coupled to the potentiometer. The method may further include the step of rotating 540, via the compression mechanism, a shaft of the potentiometer. The method may further include the step of adjusting 550, via the rotation of the shaft of the potentiometer, an impedance of the potentiometer.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. An electrical system for generating a cardiac-pulmonary resuscitation (CPR)-corrupted electrocardiogram (ECG) signal, comprising:

an ECG signal generator electrically coupled to a first contact of an automated external defibrillator (AED); and a backend circuit comprising a potentiometer electrically coupled to the ECG signal generator and a second contact of the AED, and wherein the potentiometer is configured to receive a user input to adjust an an impedance of the potentiometer, wherein the backend circuit further comprises:

a divider impedance circuit electrically coupled to the potentiometer, wherein the divider impedance circuit forms a voltage divider circuit with the potentiometer; and a reference voltage circuit electrically coupled to the divider impedance circuit and the potentiometer.

2. The electrical system of claim 1, wherein the divider impedance circuit comprises one or more resistors.

3. The electrical system of claim 1, wherein the reference voltage circuit comprises a DC voltage source.

4. The electrical system of claim 3, wherein the reference voltage circuit further comprises a regulator circuit.

5. The electrical system of claim 4, wherein the regulator circuit is a Zener diode shunt regulator circuit.

6. The electrical system of claim 1, wherein the backend circuit further comprises a potentiometer adjustment circuit electrically coupled in parallel to the potentiometer.

7. The electrical system of claim 6, wherein the potentiometer adjustment circuit comprises one or more resistors.

8. An electromechanical system for generating a cardiac-pulmonary resuscitation (CPR)-corrupted electrocardiogram (ECG) signal, comprising:

an ECG signal generator electrically coupled to a first contact of an automated external defibrillator (AED);

a backend circuit comprising a potentiometer electrically coupled to the ECG signal generator and a second contact of the AED, wherein the backend circuit further comprises:

a divider impedance circuit electrically coupled to the potentiometer, wherein the divider impedance circuit forms a voltage divider circuit with the potentiometer; and a reference voltage circuit electrically coupled to the divider impedance circuit and the potentiometer; and a compression mechanism configured to:

receive a vertical force; and adjust an impedance of the potentiometer according to the vertical force.

9. The electromechanical system of claim 8, wherein the compression mechanism comprises:

a rack having a plurality of teeth and an initial position, wherein the rack is configured to translate to a second position according to the vertical force; and a gear with a plurality of teeth engaged with the teeth of the rack such that the gear rotates according to the translation of the rack.

10. The electromechanical system of claim 9, wherein the rack is configured to translate from the second position to the initial position after the application of the vertical force.

11. The electromechanical system of claim 9, wherein the potentiometer is a rotary potentiometer having a shaft coupled to the gear such that the rotation of the gear adjusts the impendence of the potentiometer.

12. An electromechanical system for adjusting the impedance of a circuit, comprising:

a potentiometer;

a divider impedance circuit electrically coupled to the potentiometer, wherein the divider impedance circuit forms a voltage divider circuit with the potentiometer;

a reference voltage circuit electrically coupled to the divider impedance circuit and the potentiometer; and a compression mechanism configured to:

receive a vertical force; and adjust the impedance of the potentiometer according to the vertical force.

13. The electromechanical system of claim 12, wherein the compression mechanism comprises:

a rack having a plurality of teeth and an initial position, wherein the rack is configured to translate according to the vertical force; and a gear with a plurality of teeth engaged with the teeth of the rack such that the gear rotates according to the translation of the rack.

* * * * *